United States Patent [19]

Bartley

[11] 4,250,116

[45] Feb. 10, 1981

[54] PRODUCTION OF METHYL AND ETHYLAMINES WITH RHODIUM-IRON CATALYSTS

[75] Inventor: William J. Bartley, Charleston, W. Va.

[73] Assignee: Union Carbide Corporation, New York, N.Y.

[21] Appl. No.: 105,406

[22] Filed: Dec. 19, 1979

[51] Int. Cl.³ .............................................. C07C 85/00
[52] U.S. Cl. ..................................................... 564/467
[58] Field of Search ............ 260/585 R, 583 J, 583 R, 260/585 B, 585 C

[56] References Cited

U.S. PATENT DOCUMENTS

| | | | |
|---|---|---|---|
| 3,410,904 | 11/1968 | Nozaki | 260/583 R |
| 3,444,203 | 5/1969 | Kurtz | 260/583 R |
| 3,636,153 | 1/1972 | Enders et al. | 260/583 J |
| 3,646,148 | 2/1972 | Enders | 260/583 J |
| 3,726,926 | 4/1973 | Brown et al. | 260/585 R |

FOREIGN PATENT DOCUMENTS 1501891  2/1978  United Kingdom ................. 260/585 R

OTHER PUBLICATIONS

Bashkirov et al, "Iz. Akad. Nauk SSSR, Otdel. Khim Nauk", No. 4, pp. 504-506, (1958).

*Primary Examiner*—John Doll
*Attorney, Agent, or Firm*—Bernard Lieberman

[57] ABSTRACT

A heterogeneous process for selectively producing monoamines in which the nitrogen is bonded only to methyl, ethyl, hydrogen or combinations thereof which comprises contacting a mixture of carbon monoxide, hydrogen and a nitrogen-containing compound selected from the group consisting of ammonia, nitric oxide and mixtures thereof with a heterogeneous solid catalyst comprising rhodium and iron. The monoamines of the invention are formed in a collective amount of at least 50 weight percent of the total amine products of the reaction.

5 Claims, No Drawings

PRODUCTION OF METHYL AND ETHYLAMINES WITH RHODIUM-IRON CATALYSTS

This invention relates to a method of preparing monoamines in which the nitrogen is bonded only to methyl, ethyl, hydrogen or combinations thereof. More particularly, the invention relates to the preparation of such monoamines by the reaction of a synthesis gas with ammonia and/or nitric oxide in the presence of a rhodium-iron catalyst.

The synthesis of alkyl amines by the catalytic reaction of hydrogen with various combinations of reactants from among carbon monoxide or carbon dioxide, ammonia, nitrogen, aldehydes and primary amines is extensively described in the prior art. U.S. Pat. No. 3,597,438, for example, discloses the production of secondary amines by the reaction of hydrogen and an aliphatic aldehyde with ammonia or a primary amine in the presence of a rhodium metal catalyst; U.S. Pat. Nos. 3,636,153 and 3,646,148 are directed to processes for producing methylamine and dimethylamine by the reaction of hydrogen, carbon monoxide and nitrogen over a zirconium or hafnium catalyst; and U.S. Pat. Nos. 3,410,904 and 3,444,203 disclose the production of methylamines by the reaction of hydrogen, carbon monoxide and ammonia in the presence of catalysts such as copper, palladium, silver and platinum. The processes of these patents in common with most amine synthesis processes disclosed in the art are generally characterized by either the production of a wide spectrum of amine products, including many of relatively little commercial value, or the synthesis of a very specific product mixture, such as methylamines. The present invention is directed to the production of a commercially desirable product mixture, namely, low molecular weight amines which include methylamines as well as ethylamines and substituted methyl and ethyl amines. The present invention is predicated on the discovery that a catalyst containing rhodium and iron can selectively produce such monoamines to the substantial exclusion of higher carbon number amine products thereby avoiding the need for extensive product purification.

Iron-containing catalysts for the reaction of synthesis gas with ammonia are known to produce a wide spectrum of alkyl amine products. Thus, U.S. Pat. No. 2,518,754 discloses the use of Fischer-Tropsch type catalyst such as metallic iron to produce a mixture of primary, secondary and tertiary amines containing up to 12 carbon atoms, with higher alkyl primary monoamines predominating. Similarly, there is disclosed in U.S. Pat. No. 3,726,926, at column 6, Table 2, a very wide weight distribution of amine fractions which is typical for that formed by the reaction of hydrogen, carbon monoxide and ammonia in the presence of a catalyst comprising iron oxide. Similar amine product distributions formed with iron catalysts are disclosed in the following publications: Bashkiaov, et al., Doklady Akad. Nauk. S.S.S.R., 109, 774–6 (1956), [Chem. Abs., 51, 4931e (1975)]; Russian Pat. No. 133,890, Dec. 10, 1969 [Chem. Abs., 55, 14308f (1961)]; and Koelbel, et al., Angew. Chem. Internat. Ed., Vol. 5, 843 (1966), all of which publications disclose the production of alkyl monoamines ranging in chain length from 3 to greater than 11 carbon atoms (Russian Pat. No. 133,890) to as high as 40 carbon atoms (Koelbel, et al., supra.)

Catalysts containing rhodium and iron in combination are known, although not for the production of amines. For example, United Kingdom Pat. No. 1,501,891, published Feb. 22, 1978, discloses the use of Rh-Fe catalysts for the selective preparation of two-carbon atoms oxygenated compounds, particularly ethanol, from a synthesis gas mixture. A similar disclosure is found in an article by Bhasin, et al., Journal of Catalysis, Vol. 54, pp. 120–128 (1978). The use of rhodium-iron catalysts for the preparation of amines, has heretofore not been contemplated. Indeed, United Kingdom Pat. No. 436,414 which describes a process for the production of tertiary amines using hydrogenation catalysts from among Groups 1, 2, 6, 7 and 8 of the Periodic Table (iron being included in Group 8) specifically states at column 2, lines 85–87, that noble metals are not to be employed as catalysts for the particular reaction therein disclosed.

SUMMARY OF THE INVENTION

The process of the invention describes a catalyst for the selective production of monoamines in which the nitrogen is bonded only to methyl, ethyl, hydrogen or combinations thereof. The process involves contacting a heterogeneous solid catalyst comprising rhodium and iron with a mixture comprising hydrogen, carbon monoxide and a nitrogen-containing compound selected from the group consisting of ammonia, nitric oxide and mixtures of same under suitable reaction conditions to produce the desired monoamines. The process of the invention is characterized by the formation of the above-described monoamines in a collective amount of at least 50 wt. % of the total amine products formed.

PROCESS DISCUSSION

The reaction is conducted at reaction conditions of temperature, pressure, gas composition and space velocity to produce the defined monoamines in a collective amount which is at least about 50 wt. %, desirably at least 75 wt. %, and under preferred reaction conditions at least 90 wt. %, of the total amine products formed by the reaction.

Conditions of temperature, of pressure, and of gas composition are usually within the ranges that are essentially conventional for synthesis gas conversions such as those employed in the production of methanol. Thus, existing technology and equipment may generally be used to effect the reaction.

The reaction is highly exothermic, with both the thermodynamic equilibrium and the kinetic reaction rates being governed by the reaction temperature. Average catalyst bed temperatures are usually within the range of about 200°–450° C., but for optimum conversions, bed temperatures are kept within the range of about 250°–400° C., typically about 250°–350° C.

The reaction temperature is an important process variable, affecting not only total productivity but selectivity toward the amine products. Over relatively narrow temperature ranges, as for example 10° or 20° C., an increase in temperature may somewhat increase total synthesis gas conversion, tending to increase the production of amines. At the same time, however, higher temperatures favor methane production, which apparently increases more rapidly at higher temperatures than does conversion of reactants to amine products. Thus, for a given catalyst and with all other variables held constant, the optimum temperature will depend more on product and process economics than on thermodynamic or kinetic considerations, with higher temperatures tending to increase the production of amine products but disproportionately increasing the co-production of methane.

In the discussions above, the indicated temperatures are expressed as average, or mean, reaction bed temperatures. Because of the exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multistage fixed bed adiabatic reactors with interstage cooling, or relatively small catalyst particles placed in tube-and-shell type reactors with a coolant fluid surrounding the catalyst-filled tubes.

The reaction zone pressure is desirably within the range of about 15 psig to about 10,000 psig, economically within the range of about 300–5,000 psig. In general, higher reaction zone pressures increase the total weight of product obtained per unit time and likewise improve the selectivity toward amine products.

The ratio of hydrogen to carbon monoxide in the synthesis gas may vary widely. Normally the mole ratio of hydrogen to carbon monoxide is within the range of 20:1 to 1:20, preferably within the range of about 5:1 to about 1:5. Increasing the ratio tends to increase the total rate of reaction sometimes quite significantly, and has a smaller though favorable effect on the rate of production of amine products, but concurrently increases selectivity to methane.

The percent conversion of CO to products is an important process variable. At low conversions e.g., less than about one-fourth of the CO per pass and preferably not more than about one-eighth, the formation of the amines of the present invention is increasingly favored relative to other products. This conversion is conveniently achieved by employing a high space velocity correlated with other reaction variables (e.g., temperature, pressure, gas composition and catalyst). Space velocities in excess of about $10^2$ gas hourly space velocity (volumes of reactant gas, at 0° C. and 760 mm mercury pressure, per volume of catalyst per hour, commonly referred to as "GHSV") are generally employed, although it is preferable that the space velocity be within the range of about $10^3$ to about $10^6$ per hour. With regard to the amine products formed, increased space velocities favor the formation of primary and secondary amines while decreased space velocities, i.e., below $10^4$ hr.$^{-1}$, favor the formation of tertiary amines. Tertiary amines being the most stable of the amine products formed will generally be present in the product mixture in substantially greater amounts than primary and secondary amines.

The concentration of nitrogen-containing compound in the reactant gas mixture affects total productivity as well as the amine product distribution. Generally, the effect of increasing the concentration of ammonia and/or nitric oxide in the feed is to decrease the overall rate of reaction and increase the selectivity of the reaction to amines. Conversely, lower concentrations of ammonia and/or nitric oxide enhance the productivity of the reaction but disproportionately favor the production of methane and alcohols thereby lowering the reaction selectivity to amines. With regard to the amine products formed, at a fixed conversion of CO, increasing the concentration of ammonia and/or nitric oxide tends to favor the formation of primary and secondary amines while decreasing the concentration of such nitrogen-containing compounds favors the formation of tertiary amines.

The Rh-Fe catalyst of the invention comprises rhodium in combination with iron upon a support material. This is typically effected by depositing rhodium and iron onto a particulate support material and placing the supported combination into the reaction zone. On the basis of experience to date, the amount of catalyst on the support should range from about 0.01 weight percent to about 25 weight percent, based on the combined weight of the metals and the support material. Preferably, the amount of catalyst is within the range of from about 0.1 to about 10 weight percent.

The weight ratio of iron to rhodium in the catalyst should generally vary from about 0.01 to about 10 to produce alkyl amines in accordance with the invention. The particular weight ratio of iron to rhodium will affect the amine product distribution. The use of relatively low weight ratios of iron to rhodium in the catalyst, for example, a weight ratio of about 0.05 or less, results in the formation of predominantly ethylamines. Conversely, at a weight ratio of about 0.1 or greater the amine products are predominantly comprised of methylamines. The preferred weight ratio of iron/rhodium is within the range of from about 0.02 to about 1.

A relatively high surface area particulate support, e.g., one having a surface area upwards of about 1.0 square meters per gram (BET low temperature nitrogen adsorption isotherm method), is preferred, desirably upwards of about 10 square meters per gram, although surface area alone is not the sole determinative variable. Based on research to date, silica gel and titania are preferred as the catalyst base or support, with graphite, graphitized carbon, alpha alumina, zirconia, magnesia, eta-alumina, gamma-alumina, and active carbon being less desirable.

For the purpose of this invention, rhodium deposited on either particles of iron oxide or a carrier containing iron is substantially the same as rhodium and iron codeposited on any of the above support materials.

The rhodium and iron may be deposited onto the catalyst base or support by any of the techniques commonly used for catalyst preparation, as for example, impregnation from an organic or inorganic solution, precipitation, coprecipitation, or cation exchange. Conveniently, a solution of a heat decomposable inorganic or organic rhodium compound and an iron compound is appropriately contacted with the support material, and the support then dried and heated, the latter advantageously under reducing conditions, to form the finely dispersed iron-containing rhodium catalyst. Any of these materials may be deposited concurrently or sequentially.

The rhodium deposited is typically in metal form, desirably as fine discrete particles. The form of the iron component is, however, not completely appreciated. It may be chemically associated with the rhodium or it may be in a physical admixture with the rhodium. For example, the iron may be alloyed with the rhodium or not, in the form of a metal or an oxidized state of the metal, or it may be in the form of an oxide, a silicate, an aluminate, a carbonate, or the like.

DESCRIPTION OF TEST REACTOR

The reactor used in these studies was a 316 stainless steel, bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, La., on Mar. 16-20, 1969, and obtainable from AIChE at 345 East 47th St., New York, N.Y. 10017. The autoclave was internally gold plated and the interior volume was about 1 liter. A variable speed, magnetically driven fan continuously recirculated the reaction mixture over the catalyst bed. The following modifications were found to facilitate operation and inhibit run-away methanation reactions:

1. Hydrogen feed gas was introduced continuously at the bottom of the autoclave through the well for the shaft of the Magnedrive agitator.

2. Carbon monoxide feed gas was introduced continuously through a separate port at the bottom of the autoclave, in order to avoid a hydrogen-rich zone in the autoclave.

Effluent gases were removed through a port in the side of the reactor. Condensable liquid products were removed from the exit stream in a brine-cooled condenser at ca. 5° to 10° C. and were collected in a holding tank under pressure. After venting to atmospheric pressure, the non-condensable components were sampled through a rubber septum for analysis. The exit stream was then sent through a wet-test meter to determine its total volume. No external recycle was employed.

DESCRIPTION OF THE TEST PROCEDURE

The bulk volume of the weighed catalyst sample was determined and the sample was placed in the catalyst basket. The quantity of catalyst charged was 50 cc which provided an estimated reactant gas conversion of less than 10 percent. Gold-plated screens and thin layers of glass wool were placed above and below the catalyst bed to prevent circulation of solid fines. The catalyst basket was charged to the reactor, and the reactor then sealed. The sealed reactor and the process lines were pressure tested at ambient temperature and 1,000 psig using nitrogen, hydrogen, or a mixture of the two.

When the reactor was shown to be leak free, pure hydrogen was passed through the reactor at 1,000 psig and the temperature raised to about 250° C. The hydrogen and carbon monoxide flows were then adjusted at a mole ratio of 1:1 to give an approximate purge rate of 450 STP* liters/hr. corresponding to a space velocity of about 9,000 STP volumes of gas per volume of catalyst per hour. The $H_2/CO$ ratio was determined by gas chromatographic analysis of an effluent gas aliquot.

*STP refers to standard temperature and pressure defined at 0° C. and 1 atmosphere pressure.

When the desired gas composition was obtained, the reactor temperature was raised to 300° C. When conditions had stabilized, concentrated ammonia was pumped (as a liquid) to the reactor at a rate of about 24 ml./hr. using an Altex Scientific Inc. Model 100 piston pump. A period of about one hour was allowed for the reactor to reach a steady state at the new operating conditions before beginning to measure actual time of reaction. A sample of liquid product was collected over a one-hour period by cooling the product-containing gas in a brine-chilled condenser at 1,000 psig and then collecting the liquid product in a one-liter stainless steel receiver. The liquid sample was then analyzed by gas chromatography. The non-condensable gases were metered through a wet-test meter to determine their volume, and a gas sample was collected and analyzed by gas chromatography to determine its composition. The combined results are reported in Table I below.

CATALYST PREPARATION

The catalyst cited in Table I below was prepared as follows:

Rhodium trichloride and ferric chloride were dissolved in one pore volume of distilled water at ambient temperature. Davison Grade 59 Silica Gel (8-20 mesh) was placed in a vacuum flask. The top of the flask was sealed with a rubber septum, and the flask was evacuated through the side arm. A syringe needle was then used to inject the rhodium and iron solution onto the evacuated support while shaking the flask. When addition was complete, the impregnated support was allowed to stand at one atmosphere for ca. 30 minutes. It was then dried in a nitrogen atmosphere as follows: 85° C. (1 hr.); 110° C. (2 hrs.); 150° C. (2 hrs.); 300° C. (2 hrs.). The dried, impregnated support was placed in a quartz tube through which hydrogen was continuously passed. The temperature was raised to 500° C. over a 5-hour period and held at that value for 1 hour. The reduced catalyst was cooled to ambient temperature in an atmosphere of flowing hydrogen.

In order to remove significant amounts of impurities which were present in the support material as received from the manufacturer, the Davison$^{TM}$ Grade 59 silica support was initially "washed" with oxalic acid prior to being used as the catalyst support. Such treatment consisted of passing a mixture of oxalic acid, glycerine, and water in proportions of 1:1.5:2.5 by weight, respectively, through a bed of support material (length/diameter ratio of about 20 to 25) contained within a glass tube which drained through a stopcock at its base. The contents of the tube were maintained at about 90° C. by means of resistance heating wire wrapped around the exterior of the tube. About 2.5 volumes of oxalic acid solution were used to wash one volume of 8-20 mesh silica gel over a three-hour period. The material was then washed with about six volumes of distilled water at 90° C. over a period of about four hours and then dried at 350° C. for about four hours.

The chemical analysis of the silica gel for iron, aluminum, sodium and calcium impurities following the above-described treatment was as follows:

Iron as $Fe_2O_3$: 0.01% ±0.004%
Aluminum as $Al_2O_3$: 0.01% ±0.004%
Sodium as $Na_2O$: 0.01% ±0.004%
Calcium as CaO: 0.02% ±0.01%

Table I which follows provides the rate of product formation and the reaction carbon efficiency to products for the above-described rhodium-iron catalyst. As noted from Table I, the amine product mixture was comprised solely of amines in accordance with the invention.

TABLE I

PERFORMANCE DATA[a] FOR SUPPORTED RHODIUM-IRON CATALYST[b]

| Component | Rate[c] | Carbon Efficiency (%)[d] |
|---|---|---|
| Methanol | .31 | 7.4 |
| Ethanol | .27 | 8.9 |
| Propanol | .11 | 4.2 |
| Acetic Acid | .01 | 0.2 |
| Trimethylamine | .34 | 13.2 |
| Dimethylethylamine | .38 | 15.9 |
| Diethylmethylamine | .26 | 11.4 |
| N,N-Dimethylformamide | .05 | 1.6 |
| N,N-Dimethylacetamide | .04 | 1.4 |
| N,N-Diethylacetamide | .04 | 1.5 |
| N-Ethylacetamide | .07 | 2.4 |
| Butyramide | .07 | 2.4 |
| Methane | .56 | 26.7 |
| $C_2$-Hydrocarbons[e] | .04 | 2.1 |
| $C_3$-Hydrocarbons[f] | .01 | .6 |

[a]Test conditions comprised a temperature of 300° C., a reaction pressure of 1,000 psig, a 1:1 mole ratio of $H_2$/CO, a feed rate of conc. $NH_4OH$ of 24 ml./hr. and a gas space velocity of 9,000 hr.⁻.
[b]The catalyst comprised 2.5 weight percent rhodium and 0.5 weight percent iron supported on Davison ® Grade 59 silica gel.
[c]"Rate" is the rate of synthesis of the indicated product in pounds of product per cubic foot of catalyst per hour (lb/cf/hr).
[d]Percent carbon efficiency to a particular product is defined as 100 times the number of moles of carbon in that product divided by the number of moles of CO converted to products other than $CO_2$.
[e]Represents combined ethane and ethylene.
[f]Represents combined propane and propene.

What is claimed is:

1. A heterogeneous process for producing monoamines in which the nitrogen is bonded only to methyl, ethyl, hydrogen or combinations thereof which comprises contacting a mixture of carbon monoxide, hydrogen and a nitrogen-containing compound selected from the group consisting of ammonia, nitric oxide and mixtures thereof with a heterogeneous solid catalyst comprising rhodium and iron at reaction conditions which comprise a temperature of from about 200° to about 450° C. a pressure of from about 15 to about 10,000 psig and a mole ratio of hydrogen to carbon monoxide of from about 20:1 to about 1:20 such that the said monoamines are formed in a collective amount of at least 50 weight percent of the total amine products of the reaction.

2. The process of claim 1 wherein said reaction conditions include a temperature within the range of about 250°-350° C., a pressure within the range of about 300-5,000 psig and a mole ratio of hydrogen to carbon monoxide within the range of about 5:1 to 1:5.

3. The process of claim 1 wherein the conversion of CO is less than about one-fourth on a single pass basis.

4. The process of claim 1 wherein the space velocity of the mixture of hydrogen, carbon monoxide and nitrogen-containing compound is in excess of about $10^2$ GHSV.

5. The process of claim 4 wherein said space velocity is within the range of about $10^3$ to $10^6$ GHSV.

* * * * *